US010194974B2

(12) United States Patent
Kirstgen et al.

(10) Patent No.: US 10,194,974 B2
(45) Date of Patent: Feb. 5, 2019

(54) ELECTROSURGICAL INSTRUMENT

(71) Applicant: Erbe Elektromedizin GmbH, Tuebingen (DE)

(72) Inventors: Udo Kirstgen, Rottenburg (DE); Thorsten Rombach, Gomaringen (DE); Tobias Alberstetter, Mössingen (DE); Elmar Ahlburg, Trochtelfingen (DE); Volker Buntrock, Reutlingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 883 days.

(21) Appl. No.: 14/606,489

(22) Filed: Jan. 27, 2015

(65) Prior Publication Data
US 2015/0216585 A1 Aug. 6, 2015

(30) Foreign Application Priority Data
Feb. 5, 2014 (EP) .................... 14153938

(51) Int. Cl.
*A61B 18/14* (2006.01)
*A61B 18/04* (2006.01)
*A61B 18/00* (2006.01)

(52) U.S. Cl.
CPC ............ *A61B 18/14* (2013.01); *A61B 18/042* (2013.01); *A61B 2018/0091* (2013.01);
(Continued)

(58) Field of Classification Search
CPC .................. A61B 18/042; A61B 18/14; A61B 2018/00196; A61B 2018/00589; A61B 2018/0091; A61B 2018/1475
(Continued)

(56) References Cited

U.S. PATENT DOCUMENTS

| 4,580,565 A | 4/1986 | Cornell |
| 5,258,006 A | 11/1993 | Rydell et al. |

(Continued)

FOREIGN PATENT DOCUMENTS

| JP | 62-501473 A | 6/1987 |
| JP | 2002540890 A | 12/2002 |

(Continued)

OTHER PUBLICATIONS

Office action in corresponding Korean application No. 10-2015-0016481, dated Jan. 21, 2016, 17 pages.
(Continued)

*Primary Examiner* — Michael Peffley
*Assistant Examiner* — Khadijeh Vahdat
(74) *Attorney, Agent, or Firm* — Fitch, Even, Tabin & Flannery LLP

(57) ABSTRACT

An electrosurgical instrument, in particular for argon plasma coagulation, includes a handpiece 10, an electrode (11) connected to the handpiece (10), a shaft (12) which surrounds the electrode (11) and is held in the handpiece (10), and an operating mechanism (13), which comprises at least one rotary knob (14) arranged on the handpiece (10). The shaft (12) is axially movable relative to the electrode (11) and a shear force can be applied to it by operating the rotary knob (14). The handpiece (10) has a brake device which exerts a braking force on the shaft (12), and the operating mechanism (13) forms a transmission gear (15) which is connected to the shaft (12) for transferring the shear force.

15 Claims, 3 Drawing Sheets

(52) U.S. Cl.
CPC ............ *A61B 2018/00196* (2013.01); *A61B 2018/00589* (2013.01); *A61B 2018/1475* (2013.01)

(58) Field of Classification Search
USPC ..................................................... 606/28–52
See application file for complete search history.

(56) References Cited

U.S. PATENT DOCUMENTS

| | | | |
|---|---|---|---|
| 5,295,614 | A | 3/1994 | Chang |
| 5,643,292 | A | 7/1997 | Hart |
| 5,928,264 | A * | 7/1999 | Sugarbaker ...... A61B 17/00234 606/151 |
| 6,190,360 | B1 | 2/2001 | Iancea et al. |
| 6,770,071 | B2 | 8/2004 | Woloszko |
| 7,419,488 | B2 | 9/2008 | Ciarrocca et al. |
| 7,993,339 | B2 | 8/2011 | Kuehner |
| 2005/0060016 | A1 | 3/2005 | Wu et al. |
| 2005/0080476 | A1 | 4/2005 | Gunderson et al. |
| 2007/0010801 | A1 | 1/2007 | Chen et al. |
| 2009/0118727 | A1 * | 5/2009 | Pearson ............ A61B 18/1482 606/41 |
| 2009/0125023 | A1 | 5/2009 | Stephen et al. |
| 2011/0087208 | A1 * | 4/2011 | Boudreaux ........ A61B 18/1445 606/29 |

FOREIGN PATENT DOCUMENTS

| | | |
|---|---|---|
| JP | 2007504897 A | 3/2007 |
| JP | 2007508045 A | 4/2007 |
| RU | 2373871 C1 | 11/2009 |

OTHER PUBLICATIONS

Notice of Final Rejection in corresponding Korean application No. 10-2015-0016481, dated Apr. 14, 2016, 2 pages.
Notice of Final Rejection in corresponding Korean application No. 10-2015-0016481, dated Apr. 14, 2016, 5 pages.
Office action in corresponding Japanese application No. 2015-018436, dated Mar. 1, 2016, 10 pages.
Office action in corresponding Russian application No. 2015 103 664, dated Apr. 20, 2016, 15 pages.
International Search Report in corresponding European patent application 14153938.7, dated May 12, 2014, 8 pages.
Notice of Final Rejection in corresponding Korean Application No. 10-2015-0016481, dated Jun. 14, 2016, 6 pages.
First Office Action and Search in corresponding Chinese Application No. 201510044944, dated Aug. 3, 2016, 16 pages.
Second Office Action in corresponding Chinese Application No. 201510044944.3, dated Apr. 25, 2017, 7 pages.
Notice of Reasons for Rejection in corresponding Japanese Application No. 2015-018436, dated Oct. 31, 2016, 6 pages.
Decision of Refusal in corresponding Japanese Application No. 2015-018436, dated Jul. 26, 2017, 2 pages.
Office Action in corresponding European Application No. 14 153 938.7, dated Sep. 21, 2017, 6 pages.

* cited by examiner

ELECTROSURGICAL INSTRUMENT

RELATED APPLICATION(S)

This application claims the benefit of European Patent Application No. EP 14153938.7 filed Feb. 5, 2014, the contents of which are incorporated herein by reference as if fully rewritten herein.

TECHNICAL FIELD

The present invention relates to an electrosurgical instrument, in particular for argon plasma coagulation.

BACKGROUND

Electrosurgical instruments of the type referred to at the outset are used for cutting tissue or for coagulation with high-frequency alternating current. Argon plasma coagulation is a special form of electrosurgery in which non-contact transmission of the HF current takes place via ionised argon gas.

The effect of the energy input takes place with the known instrument referred to at the outset in that the exposed length of the electrode is altered. Provided for this purpose is an axially movable shaft which surrounds the electrode with an insulating effect and can be moved along the electrode in order to expose it as required.

A key requirement for such instruments is the possibility of single-handed operation. At the same time, the position of the instrument in the OP area should not change if at all possible. This means that as far as possible the grip position should be retained when operating the instrument even when the shaft is moved. In the generic instrument, this is achieved by a rotary knob which is arranged centrally in the handpiece of the instrument and can be operated with the index finger. The rotary knob actuates the shaft which can be moved axially along the electrode as a result.

A further requirement for electrosurgical instruments arises from their use in connection with a trocar which is used for inserting the electrode. At the same time, friction forces may arise between the shaft and the trocar while moving the instrument within the trocar, such forces holding back the shaft and unintentionally exposing the electrode.

SUMMARY

The object of the invention is to improve the electrosurgical instrument referred to at the outset, to the effect that the risk of injury when using the instrument in connection with a trocar or also during preparation is reduced without compromising handling of the apparatus in the process. The object of the invention is also to specify an apparatus having such an instrument.

In particular, the object is achieved by an electrosurgical instrument, in particular for argon plasma coagulation, having a handpiece and having an electrode connected to the handpiece. A shaft surrounds the electrode which is held in the handpiece. The instrument comprises an operating mechanism which has at least one rotary knob arranged on the handpiece. The shaft is axially movable relative to the electrode and a shear force can be applied to it by operating the rotary knob. The handpiece has a brake device which exerts a braking force on the shaft. The operating mechanism forms a transmission gear which is connected to the shaft for transferring the shear force.

The invention has various advantages:

The brake device improves the safety of the instrument against unintentional exposure of the electrode, for example when used together with a trocar. The braking force exerted on the shaft by the brake device prevents the shaft from being moved proximally during an application, for example during insertion through a trocar. The braking force thus leads to self-locking of the shaft which secures it against being moved unintentionally.

By operating a rotary knob, an operating force can be exerted on the shaft to alter the exposed length of the electrode. This force is normally applied by the user's finger. So as not to obstruct the user when operating the instrument, the resistance of the rotary knob should remain within a range that is felt to be ergonomically pleasant. For this, the instrument according to the invention has a transmission gear which is formed by the operating mechanism and is connected to the shaft for transferring the shear force. The transmission gear compensates the braking force applied by the brake device such that the rotary knob or the operating mechanism in general is easy to operate.

It is understood that the rotary knob is rotatable in two directions (clockwise/anti-clockwise) such that the shaft can be moved distally and proximally.

In summary, the invention increases the safety of the instrument because the shaft is secured against being moved unintentionally by the brake device. At the same time, smooth operation of the instrument is retained as the operating mechanism forms a transmission gear which converts the finger force applied by the user into the shear force acting on the shaft. In this case, the transmission gear acts like a lever arrangement which increases the shear force compared to the finger force.

The rotary knob preferably comprises a drive gear and at least one driven gear connected torque-resistantly to said drive gear, said driven gear being connected to the shaft for transferring the shear force. The diameter of the driven gear is smaller than the diameter of the drive gear. In this way, the transmission ratio necessary for smooth operation of the shaft is easily achieved. A further advantage of this embodiment is the inexpensive and safe design offered by this embodiment.

The operating mechanism may comprise a slide that is axially movable in the shear direction, said slide being connected on one hand to the shaft and on the other hand to the transmission gear. This creates a robust and simple construction that safely transmits the drive force, which is applied by the user, to the shaft.

The slide may have at least one first toothed rack which is arranged parallel to the shear direction and meshes with the driven gear. This design enables the rotary motion of the rotary knob to be easily and safely converted into a linear motion of the shaft.

For improved transmission of the force, the slide may have a second toothed rack parallel to the first toothed rack, the drive gear being arranged between the two toothed racks and being torque-resistantly connected to a further driven gear. The further driven gear is meshed with the second toothed rack.

The handpiece preferably has a retaining plate with a linear guide in which the slide is arranged so as to be axially movable. The linear guide has at least one aperture, in particular two parallel apertures, for the slide. The retaining plate enables a compact structure which requires a smaller installation space for storage of the slide.

The brake mechanism may have a clamping element, in particular a clamping ring, the clamping element being held in the handpiece and applying braking force to the shaft. The clamping element forms a passive braking means that enables easy and inexpensive construction of the instrument.

In a preferred embodiment, the operating mechanism has a locking device with which the shaft can be fixed in at least one position, in particular in a fully extended position. The locking device is particularly suitable for trocars which produce an especially high resistance during insertion of the instrument, such as reusable trocars with valve flap. The locking device is used to fix the shaft in addition to the brake mechanism so that the shaft can transfer higher axial forces without it being moved relative to the electrode.

In this case, the locking device may comprise at least a first latching means which is arranged on the slide. A second latching means is arranged on the handpiece, in particular on the mounting plate, said latching means being combinable with the first latching means for fixing the shaft. The two latching means have the advantage that they are easy to manufacture, by means of an injection moulding process for example, and at the same time they enable secure fixing of the shaft.

In an especially preferred embodiment, the electrode and the shaft are each arranged rotatably about their longitudinal axis relative to the handpiece. The electrode is guided through a sliding sleeve which connects the shaft and the electrode so as to be torque-resistant and axially movable.

This embodiment is suitable for non-rotationally symmetrical electrodes, such as spatula electrodes for example. The electrode can therefore be aligned easily in the peripheral direction. This embodiment has the advantage that rotation of the electrode is even possible when the instrument is located in the trocar. In this embodiment, the rotary motion is introduced by the shaft which is connected torque-resistantly to the electrode via the sliding sleeve. The sliding sleeve additionally has the function of establishing relative mobility between the shaft and the electrode. To do this, the sliding sleeve forms a torque-resistant and axially movable connection between the shaft and the electrode. As the shaft protrudes out of the handpiece, no additional components are necessary in order to rotate the electrode. The user simply grips the shaft and rotates it together with the electrode.

At the same time, the sliding sleeve may have profiling, at least in sections, on the inner circumference, said profiles being engaged in a positive-locking manner with the correspondingly profiled electrode, at least in sections, for transferring a torque. This design is inexpensive and safe as it is easy to manufacture an appropriately profiled sliding sleeve and safe torque transmission is achieved by the positive fit.

A cheaper and simpler construction is preferably achieved in that the sliding sleeve and the slide are rotatably and firmly connected in the axial direction of the sliding sleeve for transferring the shear force. The slide has a retaining ring which surrounds the sliding sleeve at least partially around the circumference.

In another approach, the operating mechanism has a locking device with which the shaft can be fixed in at least one position. This embodiment is not limited to the transmission gear but also functions with a simple, non-transmission gear. The safety aspect in this instrument is fulfilled by the locking device which secures the shaft against moving unintentionally even in the case of strong resistance forces.

In an approach where the electrode and the shaft are each arranged rotatably about their longitudinal axis relative to the handpiece, the electrode is guided through a sliding sleeve which connects the shaft and the electrode in a torque-resistant and axially movable manner. This makes handling easier regardless of the transmission gear because the shaft protruding out of the handpiece is simply rotated manually to align the electrode.

The invention is described below in greater detail with further particulars and with reference to the associated schematic Figures.

DETAILED DESCRIPTION

Figure 1:
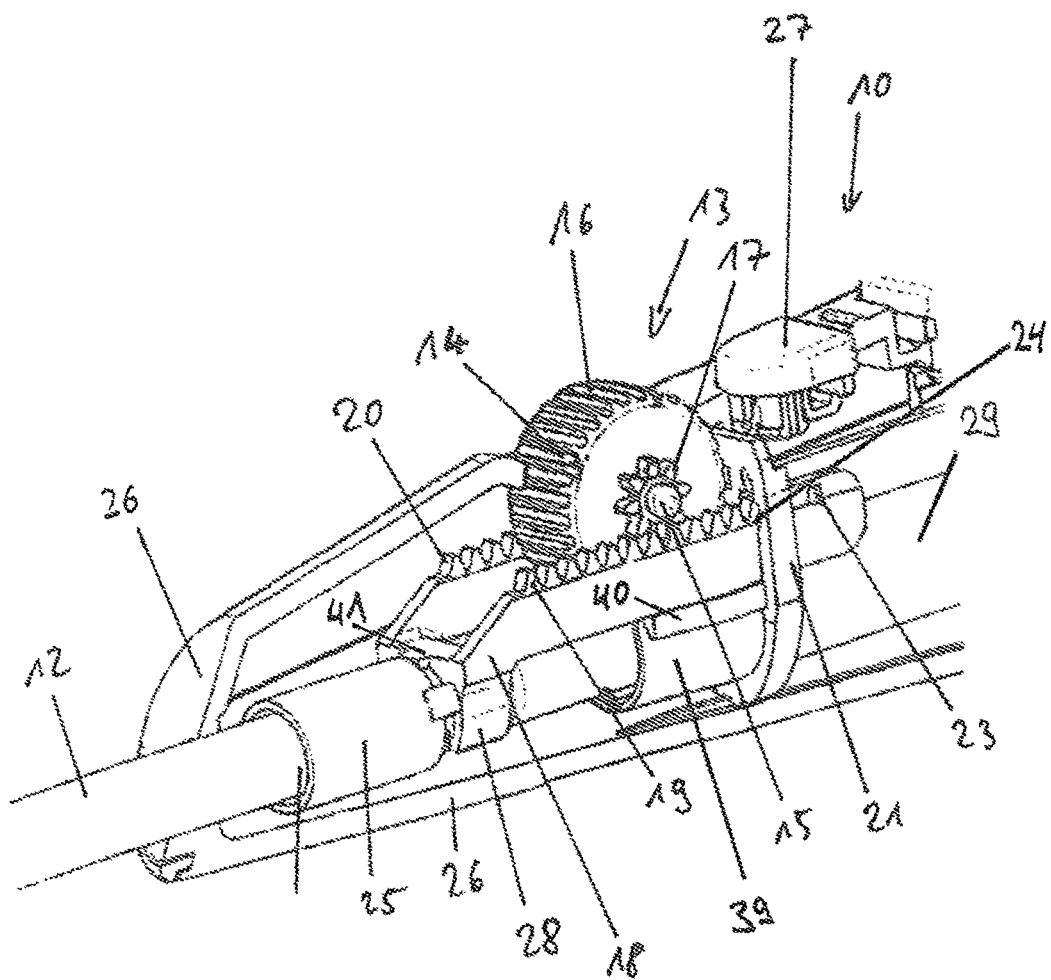
FIG. 1 is a perspective view of the instrument according to an embodiment according to the invention in which the housing is partially removed.
Figure 2:
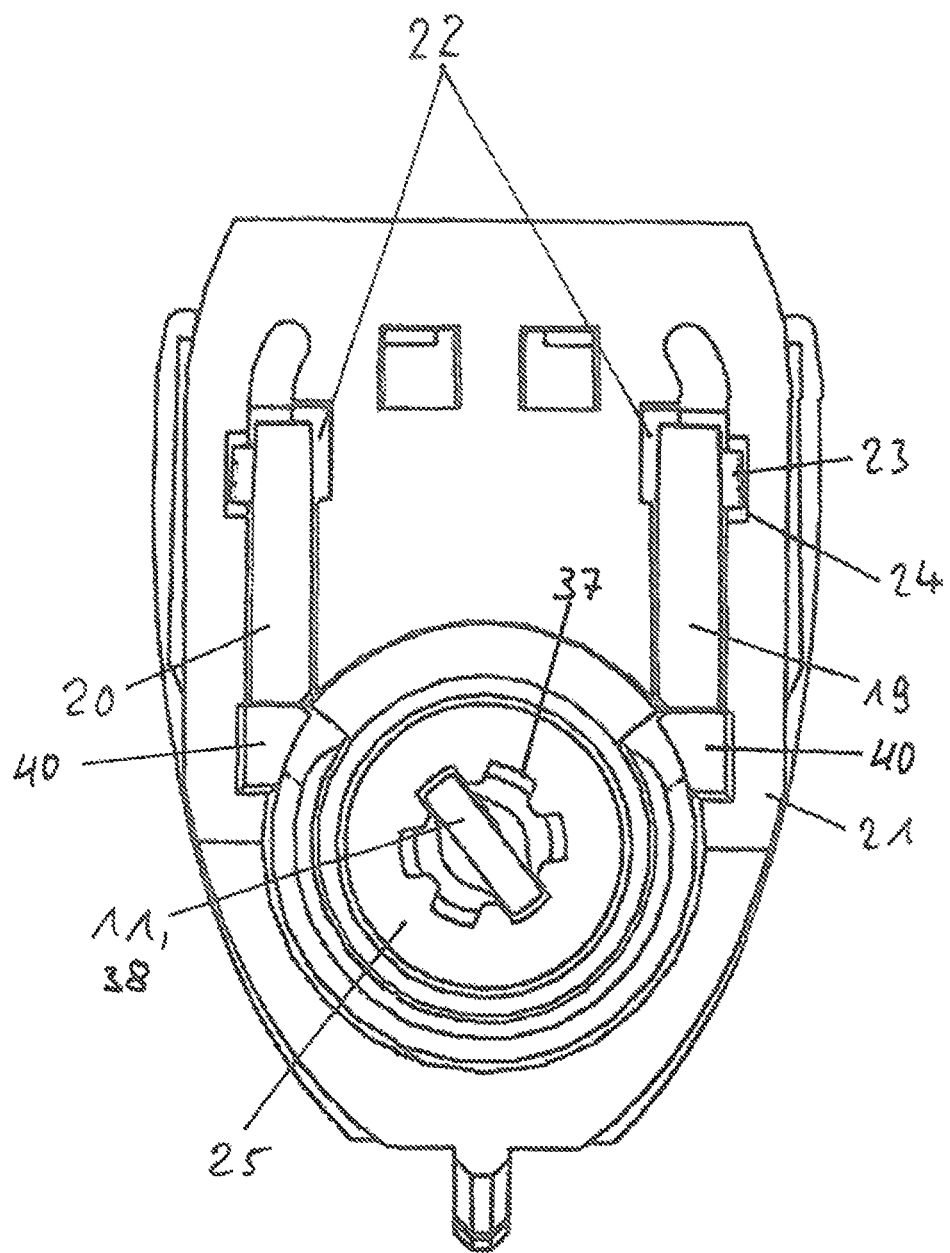
FIG. 2 is a cross-section of the instrument according to FIG. 1, wherein the rotary knob is omitted.
Figure 3:
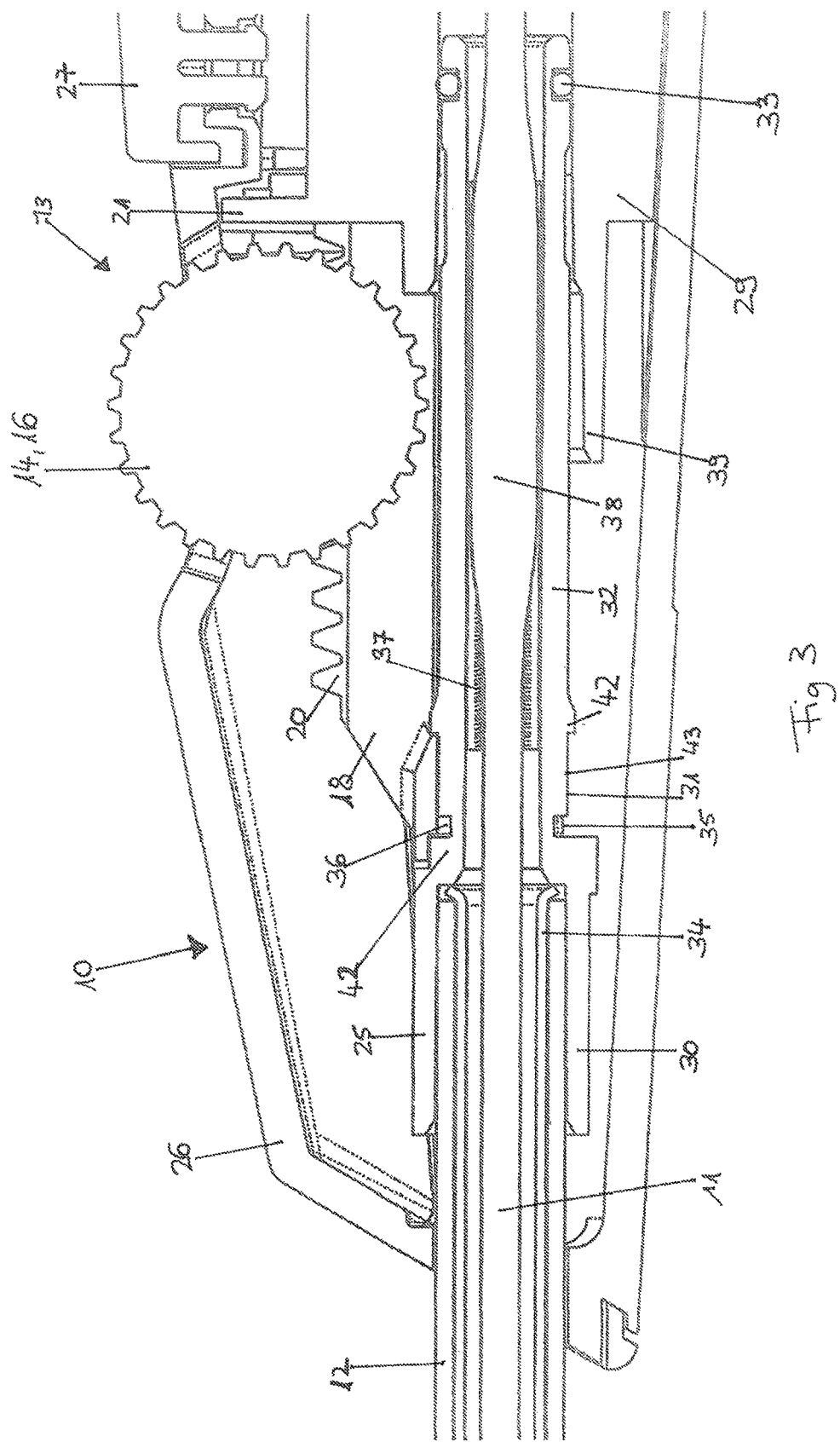
FIG. 3 is a longitudinal section of the instrument according to FIG. 1 along the central axis.

The embodiment according to FIGS. 1 to 3 shows an electrosurgical instrument that can be used for argon plasma coagulation. The invention is not limited to instruments for argon plasma coagulation but can be used generally for instruments in the field of electrosurgery in which an electrode is activated and/or controlled by moving a shaft.

The electrode 11 of the embodiment may, for example, be a hollow electrode that has a channel for the gas supply (APC electrode). Other electrodes are possible. The electrode 11 is supported in a handpiece 10. The handpiece 10 has connections or supply conductors for the electrode which enable the power supply and if necessary the gas feed to the electrode 1. One or more operating means, for example push-buttons 27 are additionally provided on the handpiece. The electrode 11 is arranged in a movable shaft 12 which protrudes distally beyond the handpiece and is held in the housing 26 of the handpiece 10 (see FIG. 3). The shaft 12 is manufactured from an insulating material and surrounds the electrode 11 at least in the region outside the handpiece 10.

The shaft 12 is movable relative to the electrode 11 such that the electrode 11 can be exposed at the distal end (not illustrated) in various positions, in particular infinitely variable, by means of an axial movement of the shaft 12. As a result, it is possible to control the region of the electrode which can come into contact with tissue when the instrument is in use. In its distal end position, the shaft 12 arranged coaxially to the electrode overlaps the electrode 11 over its entire length.

The instrument has a brake device which permanently applies a braking force to the shaft 12 and acts to secure it against moving. The braking force or even self-locking of the shaft 12 works against the resistance encountered on inserting the instrument into a trocar and prevents the shaft 12 from being unintentionally moved in the proximal direction. The advantage of securing the shaft 12 against moving also comes to bear in other situations, for example during dissection.

Specifically, the brake device has a clamping element with a friction-locked action, for example in the form of a clamping ring 33 (FIG. 3). The clamping ring 33 may be an O-ring. Other passive braking means which work against the resistance in the trocar are possible. The clamping ring 33 is at least indirectly connected to the shaft 12 and transmits the axial forces introduced into the shaft 12 to the handpiece 10, specifically into the housing 26 of the handpiece 10. For this, the shaft 12 is connected to a sliding sleeve 25. The sliding sleeve 25 and the shaft 12 are arranged coaxially. The sliding sleeve 25 can be understood as an axial extension of the shaft 12 into the handpiece 10. Clamping ring 33 is arranged in a suitable groove at the distal end of the sliding sleeve 25 in such a way that the clamping ring 33 protrudes beyond the outer circumference of the sliding sleeve 25. The clamping ring 33 is retained in the handpiece 10 and generates a braking force which works against a force that acts longitudinally on the shaft 12, for example the resistance in the trocar.

Specifically, the sliding sleeve 25 is arranged coaxially in an inner sleeve 29 which is firmly connected to the housing 26, in particular by means of a retaining plate 21. The clamping ring 33 presses against the inner circumference of the inner sleeve 29 thus generating a braking force that acts axially. The inner sleeve 29 simultaneously forms the axial guide of the sliding sleeve 25.

The clamping ring 33 or the brake device in general may be arranged at a different point on the sliding sleeve 25. It is also possible to use more than one clamping ring 33, for example two clamping rings.

To prevent the brake device from making it difficult to handle the instrument, the operating mechanism 13 forms a transmission gear 15 which is connected to the shaft 12 for transferring the shear force.

The operating mechanism 13 has a rotary knob 14 which protrudes at least in part out of the housing 26 of the handpiece 10 such that a partial circumference of the rotary knob 14 is accessible for operation with a finger. The rotary motion of the rotary knob 14 brings about the axial movement of the shaft 12. By operating the rotary knob 14 in the clockwise direction or anti-clockwise direction, the shaft can be advanced distally or retracted proximally. In other words, the shaft 12 can be moved backwards and forwards.

The function of the transmission gear 15 is that of converting the torque introduced into the rotary knob 14 in such a way that an increased shear force is applied to the shaft. The transmission gear 15 is adapted in such a way that the finger force for operating the rotary knob 14 is smaller than the self-locking of the shaft 12.

The transmission gear 15 comprises the rotary knob 14, which in turn has a drive gear 16 and at least one driven gear 17 connected torque-resistantly to said drive gear 16 (FIG. 1). The driven gear 17 is designed as a gear wheel which is coaxially connected to the drive gear 16. The drive gear 16 may have a holding means, for example in the form of a corrugation on the outer circumference, for secure movement. This ensures that the drive gear 16 can be moved precisely by means of a finger. The rotary knob 14 may be designed as a step wheel, the drive gear 16 and the driven gear 17 being formed in one piece or integrally. Alternatively, the drive gear 16 and the driven gear 17 may be joined together mechanically.

As can easily be seen in FIG. 1, the diameter of the drive gear 16 is larger than the diameter of the driven gear 17. Specifically, the diameter of the drive gear 16 is approximately 2.8 times larger than the diameter of the driven gear 17. As a result the lever ratio is approximately 1:2.8. The required finger force is therefore 2.8 times lower than the self-locking of the shaft 12. The lever ratio may be in the range of 1:2.6-3.0, in particular in the range of 1:2.7-2.9.

A further advantage of the transmission gear is that the travel path or the arc dimension traveled on the outer diameter of the drive gear 16 is also 2.8 times or a multiple of the travel path of the shaft 12. As a result it is possible to achieve a particularly accurate setting of the shaft position and therefore the degree of exposure of the electrode 11.

In the present embodiment, the outer diameter of the drive gear 16 is approx. 12.5 mm. The braking force or clamping force required for self-locking of the movable shaft 12 is approx. 4 Newton.

Conversion of the torque applied by the rotary knob 14 into a translatory motion of the shaft 12 is achieved by a slide 18 which is axially movable in a proximal and distal direction. The slide 18 forms the connection between the shaft 12 and the transmission gear 15. For this, the slide 18 has a first toothed rack 19 which is arranged parallel to the shear direction of the shaft 12. The first toothed rack 19 is meshed with the driven gear 17. Other designs for converting the rotary motion into a translatory motion are possible. In the example according to FIG. 1, the toothed rack 19 is arranged on the outside. Alternatively, an internal toothed rack may be provided which is constructed on the inside of a longitudinal slot that extends parallel to the central axis of the electrode 11. The driven gear 17 is then arranged in the longitudinal slot.

As can be gathered from FIG. 1, the slide 18 has a second toothed rack 20 which is arranged parallel to the first toothed rack 19. The drive gear 16 is arranged between the two toothed racks 19 and 20 and is torque-resistantly connected to a further driven gear 17. The further driven gear 17 (not illustrated) meshes with the second toothed rack 20. The symmetrical construction of the operating mechanism 13 leads to a uniform transmission of force and to improved safety of the instrument.

The two toothed racks 19, 20 form two arms which extend parallel to the longitudinal axis of the electrode 11. The two toothed racks 19, 20 are arranged in a linear guide which is formed by the retaining plate 21. The retaining plate 21 sits firmly in the housing 26 and has two parallel apertures 22 for the slide 18 (FIG. 2). The toothed racks 19, 20 are guided through the apertures 22 such that a safe translatory movement of the slide 18 is possible. The rotary knob 14 is arranged between the two toothed racks 19, 20 in front of the retaining plate 21 as a result of which a compact construction of the handpiece 10 is achieved.

A further improvement of safety is achieved by a locking device on the slide 18. The locking device is used to fix the shaft 12 in a specified position, in particular in the fully extended position such that the electrode 11 is overlapped as fully as possible by the shaft 12. As a result, the instrument can be used with a trocar, the friction or clamping force of which is greater than the braking force of the handpiece 10.

Unlike the locking device, which fixes the slide 18 in a specific position, the brake device is effective in any position of the slide 18 such that infinitely variable adjustment of the shaft 12 is possible.

Specifically, the locking device has a first latching means 23 which is arranged at the proximal end of each of the first and second toothed racks 19, 20. The first latching means 23 cooperates in the locked state with a second latching means 24 which is formed on the handpiece 10. Specifically, the second latching means 24 is formed on the retaining plate 21 in the form of a latch recess. The first latching means 23 may be an appropriately configured locking catch which is arranged laterally on the two toothed racks 19, 20.

The locking device improves the overall safety of the instrument according to FIGS. 1-3. It is also possible to use the locking device independently of the transmission gear and the brake device, for example if the instrument is to be used exclusively with trocars with a very high resistance, such as in the case of reusable trocars with valve flap.

A further advantage of the instrument according to FIGS. 1-3 is that the electrode 11 can be aligned in the peripheral direction, even when the shaft 12 is at least partially inserted in a trocar. For this, the electrode 11 and the shaft 12 are each arranged rotatably about their longitudinal axis relative to the handpiece 10. In other words, the electrode 11 and the shaft 12 can be rotated together. The sliding sleeve 25 through which the electrode 11 is routed is provided for this purpose. The sliding sleeve 25 connects the shaft 12 and the electrode 11. This is a torque-resistant and axially movable connection. The sliding sleeve 25 thus enables a torque to be transferred from the shaft 12 to the electrode 11. At the same time, the sliding sleeve 25 and therefore the shaft 12 joined coaxially or aligned flush with said sliding sleeve can be moved in the axial direction relative to the electrode 11.

This dual function (torque transfer and axial movability) is achieved in that the sliding sleeve 25 has profiling 37, at least in sections, on the inner circumference. The electrode 11 is correspondingly profiled in the region of the profiling 37 and is engaged in a positive-locking manner with the sliding sleeve 25 for transferring the torque. The positive-locking connection is configured such that the sliding sleeve 25 can be moved along the electrode 11 both distally and proximally.

Specifically, the sliding sleeve 25 has at least three sections, namely a distal sleeve section 30, a medial sleeve section 31 and a proximal sleeve section 32. The profiling 37 is formed in the region of the proximal sleeve section 32. The brake device, specifically the clamping ring 33, is arranged on the proximal end of the proximal sleeve section 32. The profiling 37 extends over a length that corresponds approximately to the length of the two toothed racks 19, 20. This ensures that the positive-locking connection between the electrode 11 and the profiling 37 is retained in any relative position of the sliding sleeve 25 such that the rotating function is given regardless of the respective position of the shaft 12.

As illustrated in FIG. 2, the profiling 37 is formed in the manner of a splined shaft profile. This increases the ease of assembly as the correspondingly profiled electrode 11 can be pushed into the sliding sleeve essentially regardless of its rotational position. The electrode 11 has a profile section 38 with a rectangular cross-section, as illustrated in FIG. 2. The proximal and distal end of the profile section 38 of the electrode 11 tapers in each case, as shown in FIG. 3. Distally and proximally from the profile section 38, the electrode has an essentially circular cross-section in the conventional manner. At the distal end of the electrode, the cross-section may merge into a non-rotationally symmetrical cross-section. The electrode may, for example, be a spatula electrode.

The medial sleeve section 31 has a shoulder 42 distally and proximally in each case. A retaining region 43 which is rotatably connected to the slide 18 is formed between the two shoulders 42. The retaining region 43 forms a recess between the two shoulders 42. A retaining ring 28 of the slide 18 is arranged in this recess. The retaining ring 28 is partially open and surrounds the sliding sleeve only partially around the circumference such that the retaining ring 28 can easily be clipped onto the sliding sleeve 25. The retaining ring 28 strikes against the two shoulders 42 such that axial forces or the shear force in the proximal and distal direction can be transferred for moving the shaft 12. As further security, the medial sleeve section 31 has an annular groove 35 in which a tab 36 of the retaining ring 28 is arranged. The tab 36 and the annular groove 35 are rotatable relative to each other such that the sleeve 25 is freely rotatable in the retaining ring 28. The tab 36 also transfers the shear force in both axial directions.

The retaining ring 28 is arranged between the two toothed racks 19, 20 at their distal end. Specifically, a crossbar 41 is provided which connects the distal ends of the two toothed racks 19, 20, as shown in FIG. 1. The crossbar 41 is in turn firmly connected to the retaining ring 28 or is formed in one piece. The crossbar 41 and the retaining ring 28 can also be seen as a crossbar with to retaining jaws arranged below which enclose the sliding sleeve 25 partially around the circumference.

A sufficient gap is provided between the crossbar 41 and the retaining plate 21 such that the slide 18 can be moved past the rotary knob 14 without colliding with said rotary knob 14.

The sliding sleeve 25 further comprises a distal sleeve section 30. The distal sleeve section 30 is torque-resistantly connected to the shaft 12. The connection may be made mechanically, for example by means of a fixing sleeve 34 which is arranged in the shaft 12 and is crimped on the proximal end of the shaft 12 with the sliding sleeve 25. Other fastening possibilities are conceivable. The distal sleeve section 30 forms, together with the housing 26, an axial limit stop which determines the maximum pull-out position of the shaft 12.

To support the linear guide of the slide 18, the handpiece has the previously mentioned inner sleeve 29 which is firmly connected to the retaining plate 21. The inner sleeve 29 is arranged coaxially to the electrode 11 and extends distally and proximally from the retaining plate 21, as illustrated in FIGS. 1, 2. On the distal side of the retaining plate 21, the inner sleeve 29 forms a sleeve section 39 with two guide bars 40 which extend parallel to the central axis of the inner sleeve 29.

The guide bars 40 form support surfaces for the two toothed racks 19, 20 and thus improve the stability of the linear guide.

As shown in FIG. 3, a portion of the circumferential wall of the inner sleeve 29 is removed in the region of the rotary knob 14 in order to create space for said rotary knob 14 which, apart from the circumferential segment required for finger-tip operation, is arranged in the housing 26, without colliding with the inner sleeve 29. This contributes to a compact design of the handpiece.

The rotary function of the handpiece makes it suitable for use with non-rotationally symmetrical electrodes, such as spatula electrodes, such that the handpiece is not only particularly safe and inexpensive but can also be used in different fields. The rotary function also works with other handpieces without brake device and transmission gear.

The instrument according to the invention is also additionally disclosed and claimed in connection with an electrosurgical apparatus, in particular for argon plasma coagulation.

LIST OF REFERENCE NUMBERS

10 Handpiece
11 Electrode
12 Shaft
13 Operating mechanism
14 Rotary knob
15 Transmission gear
16 Drive gear
17 Driven gear
18 Slide
19 First toothed rack
20 Second toothed rack
21 Retaining plate 22 Aperture
23 First latching means
24 Second latching means
25 Sliding sleeve
26 Housing
27 Push-button
28 Retaining ring
29 Inner sleeve
30 Distal sleeve section
31 Medial sleeve section
32 Proximal sleeve section
33 Clamping ring
34 Fixing sleeve
35 Annular groove
36 Tab
37 Profiling
38 Profiled section
39 Sleeve section
40 Guide bar
41 Crossbar
42 Shoulder
43 Retaining region

What is claimed is:

1. An electrosurgical instrument comprising:
a handpiece,
an electrode connected to the handpiece,
a shaft which surrounds the electrode and is held in the handpiece, and
an operating mechanism which comprises at least one rotary knob arranged on the handpiece,
wherein the shaft is configured to be axially movable relative to the electrode and a shear force is applied to the shaft by operating the rotary knob, wherein the handpiece has a brake mechanism configured to exert a braking force on the shaft, and the operating mechanism forms a transmission gear which is connected to the shaft for transferring the shear force;
wherein the electrode and the shaft are each arranged rotatably about their longitudinal axis relative to the handpiece, the electrode being guided through a sliding sleeve which connects the shaft and the electrode in a torque-resistant and axially movable manner.

2. The electrosurgical instrument according to claim 1, wherein the rotary knob comprises a drive gear and at least one driven gear connected torque-resistantly to said drive gear, said driven gear being connected to the shaft for transferring the shear force, the diameter of the driven gear being smaller than the diameter of the drive gear.

3. The electrosurgical instrument according to claim 1, wherein the operating mechanism comprises a slide configured to be axially movable in a shear direction of the shear force, said slide being connected on one portion to the shaft and on another portion to the transmission gear.

4. The electrosurgical instrument according to claim 3, wherein the slide comprises at least one first toothed rack arranged parallel to the shear direction and meshes with the driven gear.

5. The electrosurgical instrument according to claim 4, wherein the slide comprises a second toothed rack parallel to the first toothed rack, the drive gear being arranged between the first toothed rack and the second toothed rack and being torque-resistantly connected to a further driven gear which meshes with the second toothed rack.

6. The electrosurgical instrument according to claim 3, wherein the handpiece comprises a retaining plate with a linear guide in which the slide is arranged so as to be axially movable, the linear guide having at least one aperture for the slide.

7. The electrosurgical instrument according to claim 6, wherein the brake mechanism comprises a clamping element held in the handpiece and configured to apply the braking force to the shaft.

8. The electrosurgical instrument according to claim 6, wherein the sliding sleeve and the slide are rotatably and firmly connected in the axial direction of the sliding sleeve for transferring the shear force, the slide having a retaining ring which surrounds the sliding sleeve at least partially around the circumference.

9. The electrosurgical instrument according to claim 1, wherein the brake mechanism comprises a clamping element held in the handpiece and configured to apply the braking force to the shaft.

10. The electrosurgical instrument according to claim 1, wherein the operating mechanism comprises a locking device with which the shaft is configured to be fixed in at least one position.

11. The electrosurgical instrument according to claim 10, wherein the locking device comprises at least one first latching means which is arranged on the slide, a second latching means being arranged on the handpiece, in particular on the retaining plate, said second latching means being combinable with the at least one first latching means for fixing the shaft.

12. The electrosurgical instrument according to claim 10, wherein the locking device comprises at least one latching device arranged on the slide and a retaining plate arranged on the handpiece, wherein the at least one latching device is configured to combine with the retaining plate to fix the shaft.

13. The electrosurgical instrument according to claim 1, wherein the sliding sleeve has profiling, at least in sections, on the sliding sleeve's inner circumference, said profiling being engaged in a positive-locking manner with corresponding profiling on the electrode, at least in sections, for transferring a torque.

14. An electrosurgical instrument comprising:
a handpiece,
an electrode connected to the handpiece,
a shaft which surrounds the electrode and is held in the handpiece, and
an operating mechanism which comprises at least one rotary knob arranged on the handpiece,
the shaft being axially movable relative to the electrode and a shear force is applied to the shaft by operating the rotary knob, wherein the electrode and the shaft are each arranged rotatably about their longitudinal axis relative to the handpiece, the electrode being guided through a sliding sleeve which connects the shaft and the electrode in a torque-resistant and axially movable manner.

15. The electrosurgical instrument of claim 14, further comprising a brake mechanism configured to exert a braking force on the shaft.

* * * * *